US006316210B1

(12) United States Patent
Holzmayer et al.

(10) Patent No.: US 6,316,210 B1
(45) Date of Patent: Nov. 13, 2001

(54) GENETIC SUPPRESSOR ELEMENTS AGAINST HUMAN IMMUNODEFICIENCY VIRUS

(75) Inventors: Tanya A. Holzmayer; Stephen J. Dunn, both of Mountain View, CA (US)

(73) Assignee: Subsidiary No. 3, Inc., Wilminton, NC (US)

( * ) Notice: Subject to any disclaimer, the term of this patent is extended or adjusted under 35 U.S.C. 154(b) by 0 days.

(21) Appl. No.: 09/388,128

(22) Filed: Sep. 1, 1999

Related U.S. Application Data

(63) Continuation-in-part of application No. 09/218,755, filed on Dec. 22, 1998, which is a continuation-in-part of application No. PCT/US96/20435, filed on Dec. 20, 1996, and a continuation-in-part of application No. 08/775,703, filed on Dec. 18, 1996, which is a continuation-in-part of application No. 08/575,416, filed on Dec. 20, 1995, now abandoned.

(51) Int. Cl.[7] .......................... G01N 33/574; C12Q 1/68; C12P 21/06; A01N 43/04; C07H 21/04
(52) U.S. Cl. .................. 435/7.23; 435/6; 435/69.1; 514/44; 536/23.72
(58) Field of Search .................... 536/23.72; 514/44; 435/7.23, 6, 69.1

(56) References Cited

U.S. PATENT DOCUMENTS 5,256,534    10/1993    Butera et al. .................... 435/5

FOREIGN PATENT DOCUMENTS

| 594881 | 10/1992 | (EP) . |
| WO 9007936 | 7/1990 | (WO) . |
| WO 9012087 | 10/1990 | (WO) . |
| WO 9207071 | 4/1992 | (WO) . |
| WO 9306216 | 4/1993 | (WO) . |
| WO 9311230 | 6/1993 | (WO) . |
| WO 9410302 | 5/1994 | (WO) . |
| WO 9416060 | 7/1994 | (WO) . |
| WO 9426877 | 11/1994 | (WO) . |
| WO 9513379 | 5/1995 | (WO) . |

OTHER PUBLICATIONS

Pettit et al., 1993, Persp. Drug. Discov. Design 1:69–83.

Condra et al., 1995, Nature 374:569–571.

(List continued on next page.)

Primary Examiner—Hankyel T. Park
(74) Attorney, Agent, or Firm—McDonnell Boehnen Hulbert & Berghoff

(57) ABSTRACT

The present invention relates to genetic elements that suppress the activities of the human immunodeficiency virus (HIV). In particular, the invention relates to polynucleotides isolated from the HIV-1 genome, methods for isolating, identifying and designing such polynucleotides, and methods for using them for the protection of human cells against HIV infection and/or replication. The present invention also relates to polynucleotides that prevent tumor cell formation and the use of such polynucleotides to prevent tumorigenesis.

6 Claims, 6 Drawing Sheets

OTHER PUBLICATIONS

Torres et al., 1997, Infec. Med. 14:142–160.
Sullenger et al., 1990, Cell 63:601–608.
Sullenger et al., 1991, J. Virol 65:6811–6816.
Lisziewicz et al., 1993, New Biol. 3:82–89.
Sarver et al., 1990, Science 247:1222–1225.
Wescrasinghi et al., 1991, J. Virol. 65:5531–5534.
Dropulic et al., 1992, J. Virol. 66:1432–1441.
Yu et al., 1993, Proc. Natl. Acad. Sci. USA 90:6340–6344.
Yu et al., 1995, Proc. Natl. Acad. Sci. USA 92:699–703.
Sezakiel et al., 1991, J. Virol. 65:468–472.
Rhodes et al., 1991, AIDS 5:145–151.
Sezakiel et al., 1992, J. Virol 66:5576–5581.
Joshi et al., 1991, J. Virol 5524–5530.
Pearson et al., 1990, Proc. Natl. Acad. Sci., USA 87:5079–5083.
Modesti et al., 1991, New Biol. 3:759–768.
Trono et al., 1989, Cell 59:113–120.
Bushschacher et al., 1995, J. Virol. 69:1344–1348.
Junker et al., 1996, J. Virol. 70:7765–7772.
Woffendin et al., 1996, Proc. Natl. Acad. Sci., USA 93:2889–2894.
Moore, 1997, Science 276:51–52.
Cohen, 1997, Science 275:1261.
Gudkov & Roninson, 1996, Methods in Molecular Biology 69:229–231.
Bednarik & Folks, 1992, AIDS 6:3–16.
Poli & Fauci, 1992, AIDS Res. Human Retroviruses 9:191–197.
Foley et al., 1965, Cancer 18:522–529.
Kozak et al., 1994, Biochemie 76:815–821.
Anderson et al., 1981, Nature 290–457.
Chomym et al., 1985, Nature 314:592.
Chomym et al., 1986, Science 234:619.
Walker et al., 1992, J. Mol. Biol. 226:1051.
Fearnley et al., 1989, EMBO J. 8:665.
Pilkington et al., 1989, Biochem. 28:3257.
Koike et al., 1993, Gene 159:261–266.
Kato et al., 1989, Proc. Natl. Acad. Sci. USA 86:7861–7865.
Ou et al., 1995, J. Biol. Chem. 270:18051.
Li et al., 1996, Proc. Natl. Acad. Sci. USA 93:9606.
David et al., 1993, J. Biol. Chem. 268–9585–9592.
Tsai et al, 1991, J. Biol. Chem. 266:23053–23059.
Hochtrasser, 1995, Curr. Opin. Cell. Biol. 7:773–785.
Scherer et al., 1995, Proc. Natl. Acad. Sci. USA 92:11259–11263.
Everett et al., 1997, EMBO J. 16:556–577.
Huang et al., 1995, Science 270:1828–1831.
Zhu et al., 1996, Proc. Natl. Acad. Sci. USA 93:3275–3279.
Shimuzu et al., 1989, J. Immunol. 143:2457–2463.
Huet et al., 1989, J. Immunol. 143:798–801.
Stamenkovich et al., 1989, Cell 56:1057–1062.
Bartolazzi et al, 1996, J. Cell Biol. 132:1199–1208.
Guo & Hildreth, 1993, J. Immunol. 151:2225–2236.
Walton and Dixon, 1993, Ann. Rev. Biochem. 62:101–120.
Zolnierowiez & Hemmings, 1994, Trends Cell Biol. 4:61–64.
Nandi and Banerjee, 1995, Med. Hypothesis 45:476–480.
Ensoli et al., 1990, Nature 345:84–86.
Balliet et al., 1994, Virology 200:623–631.
Venkatesh et al., 1990, Virology 176:39–47.
Camaur et al., 1997, Virology 71:6834–6841.
Kim et al., 1996, Oncogene 13:2275–2279.
Keyse and Emslie, 1992, Nature 359:644–647.
Liscovitch and Cantley, 1994, Cell 77:329–334.
Volinina et al., 1995, EMBO J. 14:3339–3348.
Graziani et al., 1996, J. Biol. Chem. 271:6590–6593.
Garcia, 1997, C.R. Acad. Sci.III 320:505–508.
Mazerolles et al., 1997, Eur.J. Immunol. 27:2457–2465.
Borgatti et al., 1997, Eur. J. Immunol. 27:2805–2811.
Duttaroy et al., 1998, Exp. Cell Res. 238:168–176.
Uetsuki et al, 1989, J. Biol. Chem. 264:5791–5798.
Mehot et al., 1996, RNA 2:38–50.
Abramson et al., 1987, J. Biol. Chem. 262:3826–3832.
Ray et al., 1985, J. Biol. Chem. 260:7651–7658.
Rozen et al, 1990, Mol. Cell. Biol. 10:1134–1144.
Altmann et al., 1995, EMBO J. 14:3820–3827.
Methot et al., 1996, Mol. Cell. Biol. 16:5328–5334.
Milburn et al., 1990, EMBO J. 9:2783–2790.
Wozney et al., 1988, Science 242:1528–1534.
Rodier et al., 1999, Exp. Cell. Res. 249:337–348.
Rouault et al., 1992, EMBO J. 11:1663–1670.
Pulford et al., 1999, Immunology 96:262–271.
Zu et al., 1996, Blood 87:5287–5296.
Carballo et al., 1996, J. Immunol. 156:1709–1713.
Han et al., 1992, J. Virol. 66:4065–4072.
Mateer et al., 1998, J. Biol. Chem. 273:35339–35346.
Tung et al., 1997, FEBS Lett. 401:197–201.
Summers et al., 1993, Gene 136:185–192.
Frolova et al., 1994, Nature 372:701–703.
Andjelkovic et al., 1996, EMBO J. 15:7156–67.
Zhu, 1997, Arch. Biochem. Biophys. 339:210–217.
Zigman et al., 1993, Endocrinology 133:2508–2514.
Truant et al., 1999, Mol. Cell Biol, 19:1210–7.
Jenkins et al., 1998, J Cell Biol, 143:875–885.
Vodicka et al., 1998, Genes Dev, 12:175–185.
Hlavin et al., 1991, Genomics 11:416–423.
Horowitz et al., 1997, RNA 3:1374–1387.
Wang et al., 1997, J. Biol Chem. 272:17542–17550.
Flohr et al., 1992, Eur. J. Immunol. 22:975–979.
Zhu et al., 1989, J. Biol. Chem. 264–14556–14560.
Melhem et al., 1991, J. Biol. Chem. 266:17747–17753.
Mayer et al., 1998, Biochim. Biophys. Acta. 1395–301–308.
Fischer et al., 1996, J. Virol. 70:7153–7160.
Giallongo et al., 1990, Eur. J. Biochem, 190:567–573.
Giallongo et al., 1986, Proc. Natl. Acad. Sci USA 83:6741–6745.
Russell et al., 1993, DNA Cell Biol. 12:157–175.
Handen et al., 1997, FEBS Lett. 410:301–302.
Cochi et al., 1995, Science, 270:1811–1815.
Gong et al., 1998, J. Biol Chem., 271:2599–2603.
Cho et al., 1997, Biomed. Pharmacother. 51:221–229.
Sanchez et al., 1997, Electrophoresis 18:150–155.
Walsh et al., 1995, J. Leukoc. Biol. 57:507–512.
Baudet et al., 1998, Cell Death Differ, 5:116–125.
MacDonald et al., 1999, Cytogenet Genet, 84:128–129.
Fukuski, 1999, FEBS Lett. 442:83.
Lambotte et al., 1996, DNA Cell Biol., 15:769–777.
Hu et al., 1996, Proc. Natl. Acad. Sci. USA 931060–1064.
Maki et al., 1990, Proc. Natl. Acad. Sci USA 87:5440–5443.
Meroni et al., 1997, EMBO J. 15–16:2892–906.
Chinen et al., 1995, Cytogenet Cell Genet. 70:215–217.
Schilling, 1998, Virology 247:74–85.
Raboudi, et al., 1992, J. Biol. Chem. 267:11930–11939.
Liu et al., 1996, J. Biol Chem. 271:11817–11823.
Degli et al., 1994, Biochem. J. 301:161.
Friedrick et al., 1994, Eur. J. Biochem. 219–691.
Uchida et al., 1994, Int. J. Cancer 58:891.

Wyatt et al., 1995, Biochem. Pharmacol. 50:1599.
Shimomura et al., 1989, Arch. Biochem Biopys. 270:573.
Majamaa et al., 1985, Biochem. J. 229:127–133.
Yousefi et al., 1994, Proc. Natl. Acad. Sci. USA 91:10868–10872.
Lund–Johansen et al., 1996, Cytometry 25:182–190.
Coche et al, 1994, Nucleic Acids Res. 22:1322–1323.
Barre–Sinoussi et al., 1983 220:868–870.
Gallo et al., 1984, Science 224:500–503.
Teich et al., 1984 RNA Tumor Viruses, Weiss et al., eds., CSH–Press, pp. 949–956.
Varmus, 1988, Science 240:1427–1439.
Clavel et al., 1986, Science 233:343–346.
Guyader et al., 1987, Nature 326:662–669.
Dalgleish et al., 1984, Nature 312:763–767.
Klatzman et al., 1984, Nature 312:767–768.
Maddon et al., 1986, Cell 47:333–348.
Smith et al., 1986, Science 232:382–385.
Mitsuya et al., 1991, FASEB J. 5:2369–2381.
Mitsuya et al., 1990, Science 249:1533–1544.
Larder et al., 1989, Science 243:1731–1734.
Smith et al., 1987, Science 238:1704–1707.
Daar et al., 1990, Proc. Natl. Acad. Sci. USA 87:6574–6579.
Schooley et al., 1990, Ann. Int. Med. 112:247–253.
Kahn et al., 1990, Ann. Int. Med. 112:254–261.
Yarchoan et al., 1989, Proc. Vth Int. Conf. on AIDS, p. 564, MCP 137.
Erickson, 1990, Science 249:527–533.
Ventakash et al., 1990, Proc. Natl. Acad. Sci. USA 87:8746–8750.
Brady et al., 1994, Proc. Natl. Acad. Sci. USA 91:365–369.
Malim et al., 1992, J. Exp. Med. 176:1197.
Bevec et al., 1992, Proc. Natl. Acad. Sci. USA 89:9870–74.
Woffendin et al., 1994, Proc. Natl. Acad. Sci. USA 91:11581–85.
Lee et al., 1994, J. Virology 68:8254–64.
Marasco et al., 1993, Proc. Natl. Acad. Sci. USA 90:7889–93.
Chatterjee et al., 1992, Science 258:1485.
Ojwang et al., 1992 Proc. Natl. Acad. Sci. USA 89:10802–06.
Yamada et al., 1994, Gene Therapy 1:38–45.
Miller and Rosman, 1989, BioTechniques 7:980.
Miller and Buttimore, 1986, Mol. Cell. Biol. 6:2895–2902; ATCC CRL #9078.
Bednarkik and Folks, 1992, AIDS 6:3–16.
Poli and Fauci, 1992, AIDS Res. Human Retroviruses 9:191–197.
Foley et al., 1965, Cancer 18:522–29.
Nara & Fischinger, 1988, Nature 322:469–70.
Bittner et al., 1987, Methods in Enzymol. 153:516–544.
Logan & Shenk, 1984, Proc. Natl. Acad. Sci. USA 81:3655–3659.
Koike et al., 1992, Proc. Natl. Acad. Sci. USA 89:1963–1967.

GENETIC SUPPRESSOR ELEMENTS AGAINST HUMAN IMMUNODEFICIENCY VIRUS

CROSS-REFERENCE TO RELATED APPLICATIONS

This application is a continuation-in-part application of U.S. patent application Ser. No. 09/218,755, filed Dec. 22, 1998, which is a continuation-in-part of U.S. patent application Ser. No. 08/775,703, filed Dec. 18, 1996 and PCT International Application No. PCT/US96/20435, filed Dec. 20, 1996, both of which are continuations-in-part of abandoned U.S. patent application Ser. No. 08/575,416, filed Dec. 20, 1995. Each of the patent applications referred to in this section is incorporated by reference herein it its entirety.

FIELD OF THE INVENTION

The present invention relates to genetic elements that suppress the activities of the human immunodeficiency virus (HIV). In particular, the invention relates to polynucleotides isolated from the HIV-1 genome, methods for isolating, identifying and designing such polynucleotides, and methods for using them for the protection of human cells against HIV infection and/or replication.

BACKGROUND OF THE INVENTION

2.1. The Human Immunodeficiency Virus

The primary cause of acquired immunodeficiency syndrome (AIDS) has been shown to be HIV (Barre-Sinoussi et al., 1983, Science 220:868–870; Gallo et al., 1984, Science 224:500–503). HIV causes immunodeficiency in an individual by infecting important cell types of the immune system, which results in their depletion. This, in turn, leads to opportunistic infections, neurological dysfunctions, neoplastic growth, and death.

HIV is a member of the lentivirus family of retroviruses (Teich et al., 1984, RNA TUMOR VIRUSES, Weiss et al., eds., CSH-Press, pp. 949–956). Retroviruses are small enveloped viruses that contain a diploid, single-stranded RNA genome, and replicate via a DNA intermediate produced by a virally-encoded reverse transcriptase, an RNA-dependent DNA polymerase (Varmus, 1988, Science 240:1427–1439). There are at least two distinct subtypes of HIV: HIV-1 (Barre-Sinoussi et al., 1983, Science 220:868–870; Gallo et al., 1984, Science 224:500–503) and HIV-2 (Clavel et al., 1986, Science 233:343–346; Guyader et al., 1987, Nature 326:662–669). Genetic heterogeneity exists within each of these HIV subtypes.

$CD4^+$ T cells are the major targets of HIV infection because the CD4 cell surface protein acts as a cellular receptor for HIV attachment (Dalgleish et al., 1984, Nature 312:763–767; Klatzmann et al., 1984, Nature 312:767–768; Maddon et al., 1986, Cell 47:333–348). Viral entry into cells is dependent upon viral protein gp 120 binding to the cellular CD4 receptor molecule (McDougal et al., 1986, Science 231:382–385; Maddon et al., 1986, Cell 47:333–348), and a chemokine co-receptor such as CXCR4 or CCR5 (Moore, 1997, Science 276:51–52).

2.2. HIV Treatment

HIV infection is pandemic and HIV-associated diseases have become a world-wide health problem. Despite considerable efforts in the design of anti-HIV modalities, there is, thus far, no successful prophylactic or therapeutic regimen against AIDS. However, several stages of the HIV life cycle have been considered as potential targets for therapeutic intervention (Mitsuya et al., 1991, FASEB J. 5:2369–2381).

For example, virally-encoded reverse transcriptase has been a major focus of drug development. A number of reverse-transcriptase-targeted drugs, including 2', 3'-dideoxynucleotide analogs such as AZT, ddI, ddC, and ddT have been shown to be active against HIV (Mitsuya et al., 1990, Science 249:1533–1544). While beneficial, these nucleotide analogs are not curative, probably due to the rapid appearance of drug resistant HIV mutants (Lander et al., 1989, Science 243:1731–1734). In addition, the drugs often exhibit toxic side effects, such as bone marrow suppression, vomiting, and liver abnormalities.

Another stage of the HIV life cycle that has been targeted is viral entry into the cells, the earliest stage of HIV infection. This approach has primarily utilized recombinant soluble CD4 protein to inhibit infection of $CD4^{30}$ T cells by some HIV-1 strains (Smith et al., 1987, Science 238:1704–1707). Certain primary HIV-1 isolates, however, are relatively less sensitive to inhibition by recombinant CD4 (Daar et al., 1990, Proc. Natl. Acad. Sci. USA 87:6574–6579). To date, recombinant soluble CD4 clinical trials have produced inconclusive results (Schooley et al., 1990, Ann. Int. Med. 112:247–253; Kahn et al., 1990, Ann. Int. Med. 112:254–261; Yarchoan et al., 1989, Proc. Vth Int. Conf. on AIDS, p. 564, MCP 137).

Additionally, the later stages of HIV replication which involve crucial virus-specific secondary processing of certain viral proteins and enzymes have also been targeted for anti-HIV drug development. Late stage processing is dependent on the activity of a virally-encoded protease, and drugs including nelfinavir, saquinavir, ritonavir, and indinavir have been developed to inhibit this protease (Pettit et al., 1993, Persp. Drug. Discov. Design 1:69–83). With this class of drugs, the emergence of drug resistant HIV mutants is also a problem; resistance to one inhibitor often confers cross resistance to other protease inhibitors (Condra et al., 1995, Nature 374:569–571). These drugs often exhibit toxic side effects such as nausea, altered taste, circumoral parethesias, lipodystrophy and nephrolithiasis. Furthermore, these drugs also interact with many drugs commonly used to treat HIV infection (Flexner, 1998, N. Engl. J. Med. 338:1281–1292).

Antiviral therapy of HIV using different combinations of nucleoside analogs and protease inhibitors have recently been shown to be more effective than the use of a single drug alone (Torres et al., 1997, Infec. Med. 14:142–160). However, despite the ability to achieve significant decreases in viral burden, there is no evidence to date that combinations of available drugs will afford a curative treatment for AIDS.

Other approaches for developing treatment for AIDS include the delivery of exogenous genes into infected cells. One such gene therapy approach involves the use of genetically-engineered viral vectors to introduce toxic gene products to kill HIV-infected cells. For instance, replication defective vectors have been designed to introduce cell growth inhibitory genes into host cells (WO 90/12087, Oct. 18, 1980). One strategy attempted by several groups involves the delivery of the herpes simplex virus type 1 thymidine kinase (tk) toxin gene. The tk gene product is toxic to mammalian cells only in the presence of nucleoside analogs, such as ganciclovir (Ventakash et al., 1990, Proc. Natl. Acad. Sci. USA 87: 8746–8750; Brady et al., 1994, Proc. Natl. Acad. Sci. USA 91: 365–369; WO 90/07936, Jul. 26, 1990). Diphtheria toxin gene has also been used, and the gene was placed under the control of cis-acting HIV regulatory sequences (U.S. Pat. No. 5,306,631, issued Apr. 26, 1994). Others have utilized replication incompetent mutants of HIV which have the potential to express an inhibitory gene product in the presence of HIV tat (WO 94/16060, Jul. 21, 1994).

Another form of gene therapy is designed to protect virally-infected cells from cytolysis by specifically disrupting viral replication. Efforts to identify appropriate protective genes have, in large part, been based on an understanding of the molecular biology of HIV replication. A few examples of this approach are as follows.

The HIV-1 Rev gene encodes a protein that is necessary for the expression of full length HIV-1 transcripts in infected cells and the production of HIV-1 virions. Transfection with one Rev mutant known as RevM10 has been shown to protect cells against HIV infection (Malim et al., 1992, *J. Exp. Med.* 176:1197; Bevec et al., 1992, *Proc. Natl. Acad. Sci. USA* 89:9870–74). Typically, the transfectants are resistant to HIV-1 infection for about 2 weeks from the time of inoculation before resistant variants appear (Woffendin et al., 1994, *Proc. Natl. Acad. Sci. USA* 91: 11581–85).

In addition, Rev function can be interfered with by producing an excess of the binding site of the Rev protein, termed Rev Response Element (RRE), which prevents the binding of Rev to RRE of viral transcripts. A "decoy" which consisted of achimeric RNA composed of an RRE and a tRNA prevented infection of cultured cells for a period of greater than about 40 days (Lee et al., 1994, *J. Virol.* 68:8254–64).

Alternatively, fusion proteins capable of binding to viral env proteins have been made to prevent the production of HIV-1 virions. Examples include a fusion protein composed of CD4 and a lysosomal targeting protein procathepsin D, and an anti-env Fv which is secreted into the endoplasmic reticulum (Lin et al., WO 93/06216; Marasco et al., 1993, *Proc. Natl. Acad. Sci. USA* 90:7889–93).

Antisense polynucleotides have also been designed to complex with and sequester the HIV-1 transcripts (Holmes et al., WO 93/11230; Lipps et al., WO 94/10302; Kretschmer et al., EP594,881; and Chatterjee et al., 1992, *Science* 258:1485). Furthermore, an enzymatically active RNA, termed ribozyme, has been used to cleave viral transcripts. The ribozyme approach to forming an HIV-1 resistant hematopoietic cell line has been reported (Ojwang et al., 1992, *Proc. Natl. Acad. Sci. USA* 89:10802–06; Yamada et al., 1994, Gene Therapy 1:38–45; Ho et al., WO94/26877; and Cech and Sullenger, WO 95/13379).

Roninson et al. described a method for isolating genetic fragments from the HIV-1 genome capable of protecting a cell from HIV-1 infection (U.S. Pat. No. 5,217,889 and WO 92/07071). The method involves the preparation of an expression library known as a Random Fragment Expression (RFE) library that contains random sequence fragments of the HIV-1 genome. Gene fragments referred to as HIV-1 Genetic Suppressor Element (HIV-1 GSE) are then selected from the RFE library following an extensive selection procedure. The selection step involves transfection of the RFE library into a cell line to which HIV-1 infection is normally cytotoxic. However, the low sensitivity of this selection step greatly limits the practical use of the procedure. Moreover, no specific GSE sequences were reported using this method that were capable of suppressing HIV-1 infection.

2.3. Tumorigenesis

It has been reported that overexpression of the hdm2 protein drives oncogenesis through antagonism of the p53 tumor suppressor protein. Binding of hdm2 to p53 promotes the degradation of p53. Several recent reports focus on the requirement for the hdm2 protein to actively shuttle between nucleus and cytoplasm in order to exert inhibition of p53 (Lain et al., 1999, *Exp. Cell Res.* 248(2):457–472). An inhibitor of nuclear expert activates the p53 response and induces the localization of HDM2 and p53 to U1A-positive nuclear bodies associated with the PODs (Roth et al., 1998, *EMBO J.* 15:554–564). Nucleo-cytoplasmic shuttling of the hdm2 oncoprotein regulates the levels of the p53 protein via a pathway used by the human immunodeficiency virus rev protein (Tao et al., 1999, *Proc. Natl. Acad. Sci. USA* 96:3077–3080). P19(ARF) stabilizes p53 by blocking nucleo-cytoplasmic shuttling of Mdm2 (Tao et al., 1999, *Proc. Natl. Acad. Sci. USA* 96:6937–6941). Thus, shuttling of the hdm2 protein apparently depends on a nuclear export pathway that overlaps, or is identical to, that utilized by the HIV rev protein. Furthermore, the p19(ARF) tumor suppressor stabilizes p53, thereby inhibiting tumorigenesis, by interfering with this nucleo-cytoplasmic shuttling.

Thus, there remains a need to isolate and identify genetic suppressor elements that are involved in the inhibition of HIV infection or tumorigenesis.

SUMMARY OF THE INVENTION

The present invention relates to specific HIV-derived polynucleotides herein referred to as GSEs that suppress HIV infection and/or replication in human cells, methods for isolating and identifying such polynucleotides, methods for designing such polynucleotides, and methods for using them in the prevention or treatment of HIV infection.

The invention is based, in part, on the Applicants' discovery that nucleotide fragments can be isolated from the HIV-1 genome, based on their ability to suppress the activation of latent HIV-1 in a CD4$^+$ cell line or on their ability to prevent cells from productive infection by HIV-1. In this connection, any cellular or viral marker associated with HIV replication can be used to monitor the activation of latent HIV or productive infection of cells. A number of novel HIV-1 GSE polynucleotides are selected on the basis of their ability to sustain CD4 expression by the induced cells, and several of such sequences are further shown to protect uninfected T cells from productive infection by HIV-1. The GSEs may function in the form of an RNA product or protein product, both of which are within the scope of the invention. Another exemplary marker is the intracellular p24. Replication of HIV in susceptible cells is associated with accumulation of intracellular p24, concomitant with down modulation of surface CD4. The expression of GSEs capable of interfering with productive infection should result in enrichment of protected cells displaying the CD4 +, p24$^-$ phenotype. Such cells can be separated by FACS from infected population.

This invention is also based upon the discovery that isolated GSEs cluster around narrowly defined regions of the HIV-1 genome, particularly, the surprising discovery that inhibitory or protective clusters of GSEs were also isolated from previously untargeted regions (RT and nef). Preferred embodiments of the invention provide methods for designing GSEs based upon the consensus sequences of such GSE clusters.

A wide range of uses are encompassed by the invention, including but not limited to, AIDS treatment and prevention by transferring GSE into HIV-1-susceptible cell types. For example, GSE may be transferred into T cells or hematopoietic progenitor cells in vitro followed by their engraftment in an autologous, histocompatible or even histoincompatibile recipient. In an alternative embodiment of the invention, any cells susceptible to HIV infection may be directly transduced or transfected with GSE in vivo.

One embodiment of the present invention are GSEs that overlap with the HIV gene rev and the use of such GSEs to prevent tumorigenesis.

BRIEF DESCRIPTION OF THE DRAWINGS

FIG. 5A: CEM-ss cells containing IGX-117 (vpr/tat sense, SEQ ID NO:9), IGX-201 (RRE antisense, SEQ ID NO:15) and controls were infected with a $TCID_{50}$ of 500 of $HIV1_{SF2}$.

DETAILED DESCRIPTION OF THE INVENTION

Figure 1:
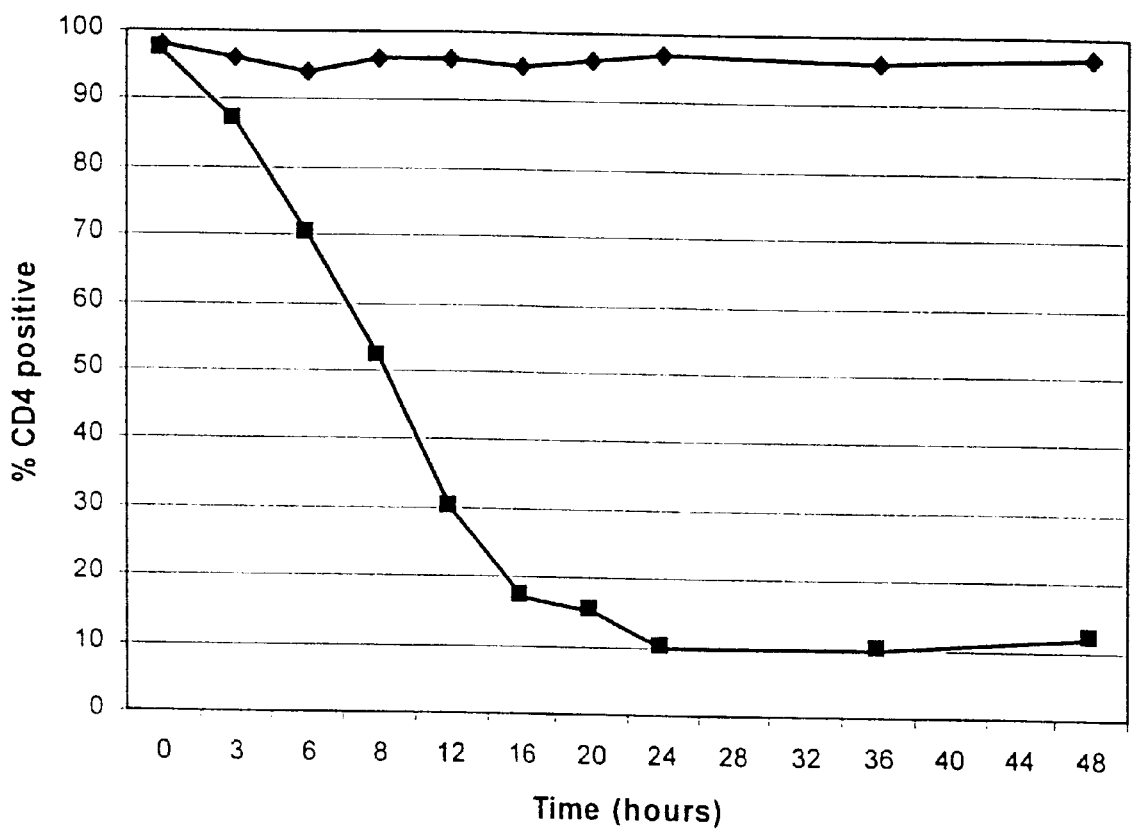
FIG. 1. Percentage of $CD4^+$ OM10.1 cells diminishes after TNF-α induction; TNF-induced cells, -■-; uninduced cells, -♦-.

The present invention relates to specific HIV-derived polynucleotides identified by an improvement of the method disclosed by Roninson et al. in U.S. Pat. No. 5,217,889. More specifically, the improvement of the method includes the use of a cell line containing a latent and inducible HIV-1 provirus such as OM10.1. In addition, the improvement also encompasses the use of a marker associated with HIV infection such as CD4 to select for polynucleotides from an HIV-1 RFE library that effectively suppress HIV-1 infection. The GSEs selected by this procedure are also capable to protect uninfected cells from HIV infection. The rev GSEs selected by this procedure are also capable of preventing tumor cell formation.

In another aspect of the invention, GSEs are isolated based upon their ability to prevent cells from productive infection by HIV-1.

Generally, the method of the invention includes the steps of: 1) randomly fragmenting cell-derived cDNA into fragments; 2) inserting the fragments into expression vectors such that the fragments are transcribed and translated to form an expression library; 3) transferring the expression library into a population of cells containing an inducible latent HIV-1 provirus or cells susceptible to HIV infection; 4) selecting a subpopulation of cells which contain a subset of the expression library enriched for HIV-1 GSEs by monitoring the expression of a cellular or viral marker associated with HIV infection; and 5) recovering the GSEs from the selected cell population. In preferred embodiments, the cell-derived cDNA is randomly-fragmented into 100–700 base pair (bp) fragments. The method further includes repetition of the aforementioned steps with a secondary or tertiary library so that many rounds of successive selection can be performed. The selection of GSEs can be performed by monitoring the continued expression of a cellular marker such as CD4 or the decreased expression of a viral marker such as p24 or gp120 using an antibody.

The invention is discussed in more detail in the subsections below, solely for purposes of description and not by way of limitation. For clarity of discussion, the specific procedures and methods described herein are exemplified using OM10.1 cells, CEM-ss cells, tumor necrosis factor-alpha (TNF-α), an anti-CD4 antibody, and an anti-p24 antibody, but they are merely illustrative for the practice of the invention. Analogous procedures and techniques are equally applicable to isolating GSE from different subtypes of HIV, utilizing any cell line containing an inducible latent provirus or any cell line or freshly isolated cell population susceptible to HIV infection, and any marker associated with HIV infection that can be easily assayed.

1.1. Preparation and Transfection of an HIV-1 GSE Library

An HIV RFE library can be constructed from the DNA of a plasmid or multiple plasmids that contain an HIV provirus insert. HIV proviral DNA is first treated with enzymes to produce randomly cleaved fragments. This can be conveniently performed by DNase I cleavage in the presence of $Mn^{++}$ (Roninson et al., U.S. Pat. No. 5,217,889, column 5, lines 5–20). Thereafter, the randomly cleaved genomic DNA are size fractionated by gel electrophoresis. Fragments of between 100 and 700 bp are the preferred lengths for constructing RFE libraries. Single strand breaks of the size-selected fragments are repaired, e.g., by Klenow or T4 polymerase, and ligated with 5' and 3' adaptors.

The 5' and 3' adaptors are selected to have non-cohesive restriction sites so that each fragment can be inserted into an expression vector in an oriented fashion. Further, the 5' adaptor contains at least one start (ATG) codon to allow the translation of the fragments which contain an open reading frame in the correct phase.

After ligation with the adaptors the fragments are inserted into appropriate expression vectors. Any expression vector that results in efficient expression of the fragments in host cells can be used. In a preferred embodiment viral based vectors such as the retroviral vectors LXSN and a modified LSXN vector, LXSNgfr, are exemplified (Miller and Rosman, 1989, *BioTechniques* 7:980). Alternatively, adeno-associated virus vectors may also be used for this purpose.

When viral-based vectors are used, the ligated vectors are first transfected into a packaging cell line to produce viral particles. For retroviral vectors, any amphotropic packaging line such as PA317 (Miller and Buttimore, 1986, *Mol. Cell. Biol.* 6:2895–2902; ATCC CRL #9078) or BING may be used to efficiently produce virus. In a preferred embodiment of the invention, the viral vector also contains a selectable gene, such as the $neo^r$ gene or a truncated nerve growth factor receptor (NGFR) gene, which allow isolation of the cells that contain the vector.

The number of independent clones present in each GSE expression library may vary. In a preferred embodiment, libraries of about $5 \times 10^4$ to $10^6$ independent clones may be used.

1.2. Selection of GSE in HIV-Infected Cells

In a specific embodiment by way of example, OM10.1 cells are used to select for GSEs, and they are maintained in conventional tissue culture as described in Butera (U.S. Pat. No. 5,256,534). The purpose of using OM10.1 cells for the selection of HIV-1 GSEs is that they contain a latent HIV-1 provirus which is inducible by TNF-α. Other cell lines may be similarly engineered with an inducible HIV provirus. Examples of cell lines that are infected with latent HIV include, but are not limited to, U1, U33, 8E5, ACH-2, LL58, THP/HIV and UHC4 (Bednarik and Folks, 1992, *AIDS* 6:3–16). A variety of agents have been shown to be capable of inducing latent HIV-infected cells, and these include TNF-α, TNF-β, interleukins-1, -2, -3, -4 and -6, granulocyte-macrophage colony stimulating factors, macrophage-colony stimulating factors, interferon-γ, transforming growth factor-β, PMA, retinoic acid and vitamin D3 (Poli and Fauci, 1992, *AIDS Res. Human Retroviruses* 9:191–197).

The HIV-infected cells may be transduced with the HIV-1 RFE library by any technique well known in the art that is appropriate to the vector system employed. In one embodiment of the invention, the viral vector also contains a selectable marker in addition to a random fragment of the HIV-1 genome. A suitable marker is the neo$^r$ gene, which permits selection by the drug G-418. In alternative embodiments, the multiplicity of infection of the virions of the library is adjusted so that pre-selection for cells that are transduced by the vector is not needed.

In the case of OM10.1 cells, the transduced population is treated with 10 U/ml TNF-α for a period of 24–72 hours and preferably about 24 hours according to the method of Butera. The activation of the latent HIV-1 provirus in OM10.1 can be detected by the suppression of the cell surface CD4. It is believed that viral protein gp120 binds to CD4 in the cytoplasm, which prevents subsequent expression of CD4 on the cell surface. Clones that are resistant HIV replication continue to express cell surface CD4. Such clones can be selected by cell sorting using any conventional antibody staining technique for CD4 and a fluorescence activated cell sorter (FACS).

After selection for continued CD4 expression, the OM10.1 cells harboring putative GSE and sorted after TNF-α induction are used to purify genomic DNA and the inserts amplified by the polymerase chain reaction (PCR). Optionally, the selected OM10.1 cells can be re-cultured under the selection conditions for the marker gene, e.g., in G-418, to ensure that the cells have retained the GSE derived from the HIV-1 RFE library.

The fraction of CD4$^+$ cells that have been transduced with an HIV-1 RFE library can be compared with cells transduced with an expression library consisting of the vector only. An increased relative difference between the HIV-1 RFE library and the control library can be found with each additional round of TNF-α induction. Thus, in the preferred embodiment of the invention there are at least two cycles of induction, selection and reculturing before the HIV-1 GSE are recovered from the cells for further characterization.

1.3. Recovery GSE From the Selected Cells

After selection, specific GSE sequences can be recovered from cells that continue to express CD4 following induction of the latent HIV provirus by TNF-α. The HIV-1-associated GSEs in this population are recovered by amplification in PCR using the primers according to the sequence of the linkers.

The recovered GSEs can be introduced into an expression vector as discussed in Section 5.1, supra. The resultant HIV-1 GSE expression library is known as a secondary library. The secondary library may utilize the same or a different vector from that used for the construction of the primary library. The secondary library may be transduced into another cell population and the resultant population selected, recultured and processed as described herein.

Additionally, each individually recovered element can be inserted into cloning vectors for determining its specific nucleotide sequence, its orientation and the portion of HIV genome from which it is derived. Concurrently, the isolated GSEs can be analyzed to determine their minimal core sequences and tested for their ability to protect previously uninfected cells from HIV infection.

In addition to the sequences depicted in SEQ ID NOS: 1–25, nucleotide sequences capable of hybridizing to these sequences or their complementary sequences under highly or moderately stringent hybridization conditions are well within the scope of the invention. Highly stringent hybridization conditions may be defined as hybridization to filter-bound DNA in 0.5 M NaHPO4, 7% sodium dodecyl sulfate (SDS), 1 mM EDTA at 65° C., followed by washing in 0.1×SSC/0.1% SDS at 68° C. (Ausubel F.M. et al., eds, 1989, CURRENT PROTOCOLS IN MOLECULAR BIOLOGY, Vol. I, Green Publishing Associates, Inc., and John Wiley & Sons, Inc., New York at p.2.10.3). Less highly stringent conditions, such as moderately stringent conditions, may be defined as hybridizations carried out as described above, followed by washing in 0.2×SSC/0.1% SDS at 42° C. (Ausubel et al., 1989, supra).

1.4. Determination of Core Sequences of GSE

Figure 3:
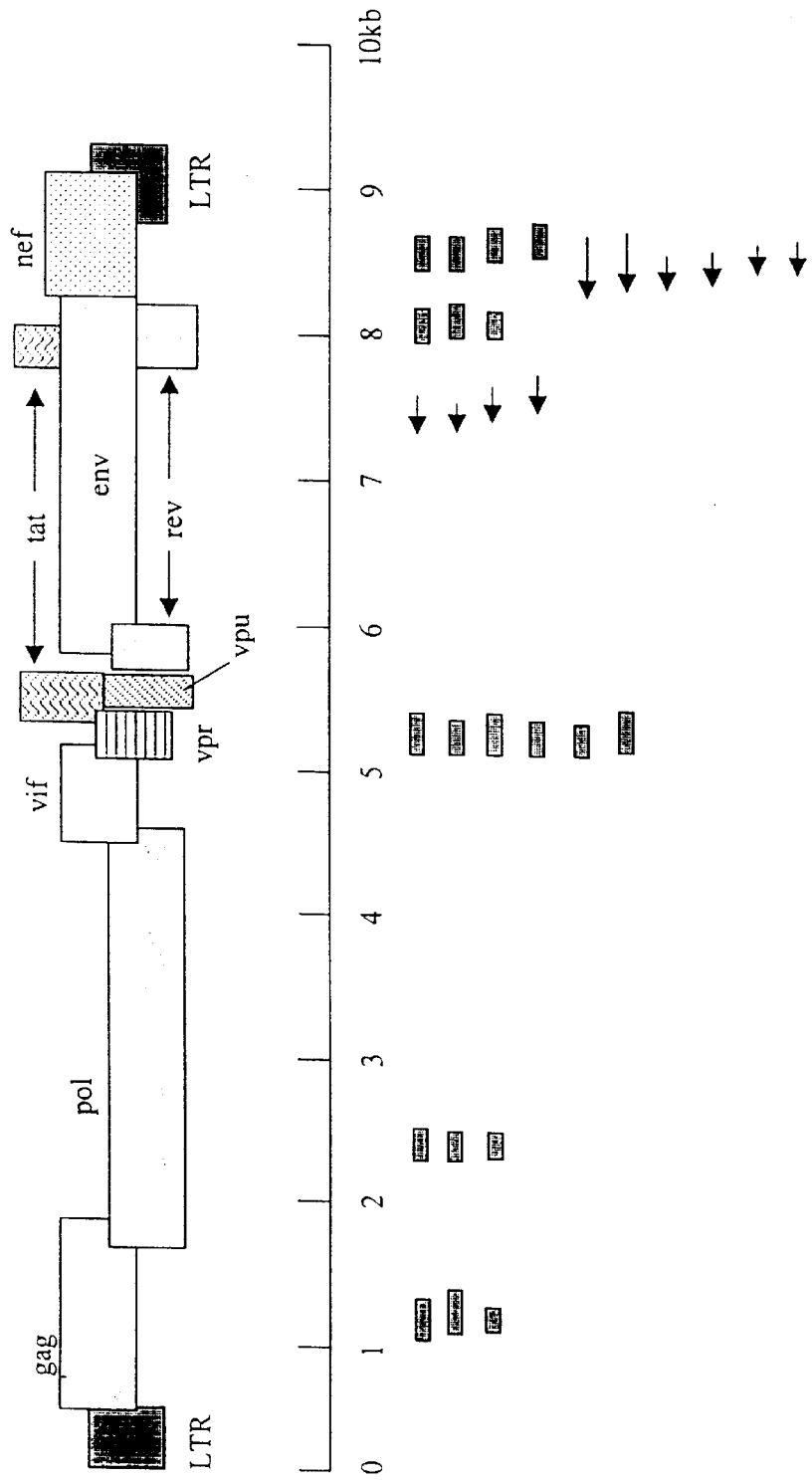
FIG. 3. Location of isolated HIV GSE on the HIV-$1_{BRU}$ genome. Arrows indicate antisense orientation elements, while shaded boxes indicate sense orientation elements. Scale of the HIV-1 genome is in kilobases.
Figure 4:
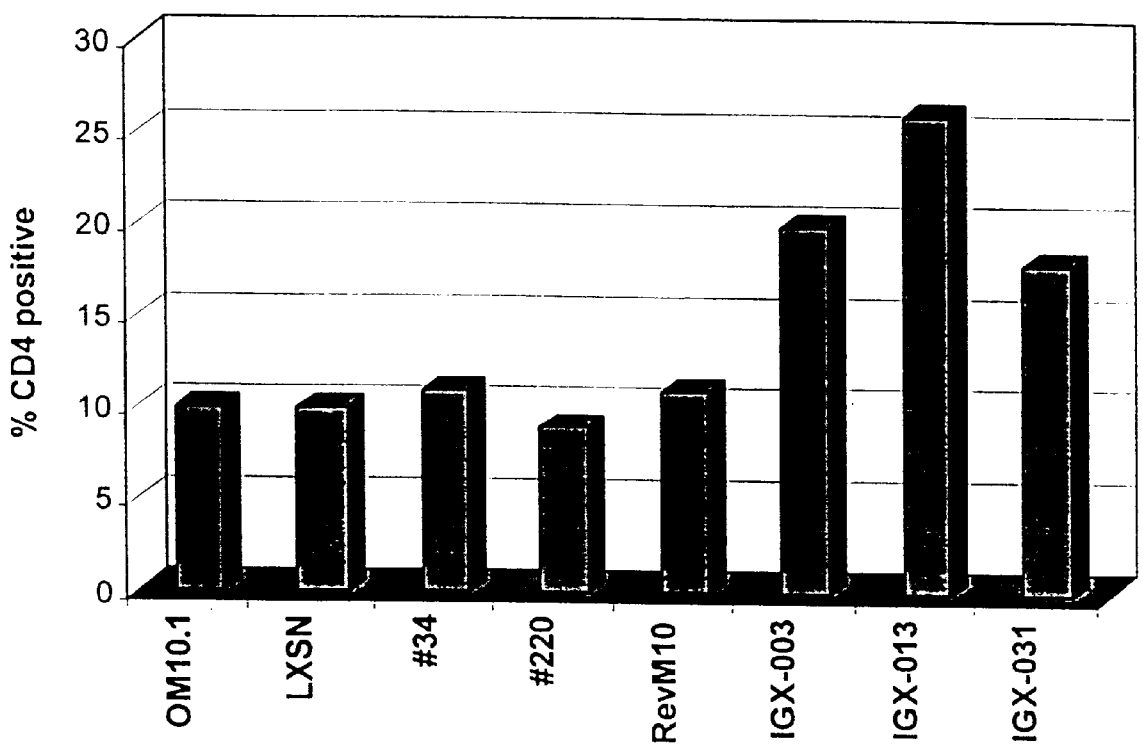
FIG. 4. CD4 retention levels of OM10.1 cells containing GSEs after TNF-α induction.

The present invention also includes methods for determining the core sequence of each GSE. This may be done by comparing overlapping sequences of independently derived GSEs. FIG. 3 depicts a number of clusters of independently derived GSEs. A surprising discovery of the invention is that isolated GSEs are clustered around narrowly defined regions of the HIV-1 genome. In addition, clusters of GSEs from previously untargeted regions (i.e., reverse transcriptase and nef) were also isolated. In FIG. 3, a number of GSEs selected on the basis of their ability to prevent productive infection are clustered in the region (RT) with coordinates 2426–2511 of the HIV-1 isolate BRU (GenBank accession number K02013). Such GSEs also showed inhibitory effects upon in virally-infected cells (FIG. 4). One of skill in the art would appreciate that sequences selected from this region are expected to be active in preventing productive infection and in inhibiting induction of latently infected cells. Similarly, a number of GSEs are clustered around the region 8195–8599 of the HIV-1 genome in both sense and antisense orientation. It would be apparent to those of skill in the art that nucleotides containing sequences selected from this region are likely to be active in preventing productive infection and/or inhibiting virus induction in latently infected cells.

Depending upon the mechanisms of action of specific GSEs, the length of GSE sequences may affect their ability of inhibiting HIV-1 infection. The sequences selected from the regions of the viral genome depicted in FIG. 3 are preferably at least 25 nucleotides, more preferably at least 50 nucleotides, and most preferably at least 100 nucleotides in length.

Alternatively, GSEs may be altered by additions, substitutions or deletions and assayed for retention of HIV-suppressive function. Alterations in the GSE sequences may be generated using a variety of chemical and enzymatic methods which are well known to those skilled in the art. For example, oligonucleotide-directed mutagenesis may be employed to alter the GSE sequence in a defined way and/or to introduce restriction sites in specific regions within the sequence. Additionally, deletion mutants may be generated using DNA nucleases such as Bal 31 or Exo III and S1 nuclease. Progressively larger deletions in the GSE sequences may be generated by incubating the DNA with nucleases for increased periods of time (See Ausubel et al., 1989 CURRENT PROTOCOLS FOR MOLECULAR BIOLOGY, for a review of mutagenesis techniques).

The altered sequences may be evaluated for their ability to suppress expression of HIV proteins such as p24 in appropriate host cells. It is well within the scope of the present invention that any altered GSE sequences that retain their ability to suppress HIV infection may be incorporated into recombinant expression vectors for further use.

1.5. Protection of Uninfected Cells by GSE Against HIV-1 Infection

In order to confirm that the selected GSEs can protect uninfected cells from HIV-1 infection, the GSEs may be transferred into HIV susceptible host cells, followed by HIV infection. Protection experiments can be performed in any cell type that takes up the potential HIV-1 GSEs and which is otherwise susceptible to HIV infection. In a preferred embodiment by way of example, the CEM-ss cell line is used (Foley et al., 1965, *Cancer* 18:522–29). The use of CEM-ss cells as targets for quantitative infectivity of HIV-1 has been described by Nara & Fischinger (1988, *Nature* 322:469–70). Other cell lines that are susceptible to HIV infection include, but are not limited to, HUT-78, H9, Jurkat E6-1, A3.01, U-937, AA-2, HeLa CD4$^+$ and C8166.

The test of the potential HIV-1 GSEs can be performed using the same expression vector system as that employed in the RFE library transduction of cells during initial selection steps. In other embodiments, the vector system can be modified to achieve higher levels of expression, e.g., linkers can be employed to introduce a leader sequence that increases the translational efficiency of the message. One such sequence is disclosed by Kozak, 1994, *Biochemie* 76:815–821.

Another way of testing the effectiveness of a GSE against HIV is to determine how rapidly HIV-1 variants develop that can negate the effects of the potential HIV-1 GSE. Such a test includes infection of a culture of susceptible cells such as CEM-ss cells at a low multiplicity of infection and repeatedly assaying the culture to determine whether and how quickly HIV-1 infection becomes widespread. The range of useful multiplicities of infection is between about 100 to 1000 tissue culture infectious units ($TCID_{50}$) per $10^6$ CEM-ss cells. The $TCID_{50}$ is determined by an endpoint method and is important for determining the input multiplicity of infection (moi).

A parameter that correlates with the development in the test culture of HIV-1 strains that are resistant to the effects of the potential HIV-1 GSE is the fraction of cells that are infected in the culture. This fraction can be determined by any means. Immunofluorescent staining with an antibody specific for the HIV-1 p24 antigen of fixed permeabilized cells is a convenient method for determining the fraction of cells that is infected. Commercially available reagents are suitable for performing such tests (Lee et al., 1994, *J. Virol.* 68:8254–8264).

In Section 6.2, infra, GSEs were tested for their ability to protect CEM-ss cells from infection with HIV-1 strains $SF_2$ and IIIB. Uninfected cells were transduced with a LXSN construct containing either an irrelevant DNA or a GSE sequence. Non-transduced cells were eliminated by exposure to the selection agent, G-418. The percentage of p24$^{30}$ cells was determined at specific time points post infection. The results demonstrate that GSEs tested are able to protect a productive HIV-1 infection in susceptible host cells.

1.6. Uses of GSE to Suppress HIV-1 Infection

Another aspect of the present invention is to use the isolated GSEs against HIV infection prophylactically or therapeutically. In this connection, GSE operably linked to a regulatory sequence such as a promoter that controls its expression may be transferred in vitro into any HIV-susceptible host cells such as CD4$^+$T cells or hematopoietic progenitor cells such as CD34$^+$ cells obtained from bone marrow or mobilized peripheral blood, by any DNA transfer techniques well known in the art such as electroporation, transfection or transduction, followed by transplantation of the cells into a recipient. When the GSE-containing progenitor cells differentiate in vivo, the progeny cells express the GSE and become resistant to HIV.

Alternatively, GSEs may be directly administered in vivo using a gene therapy expression vector. In particular, anti-HIV GSEs can be delivered or transferred into CD4$^+$ T cells in both HIV-infected or uninfected individuals to protect against development of HIV infection. GSEs can also be transferred into stromal cells, including macrophages.

Expression vectors derived from viruses such as retroviruses, adeno-associated virus, herpes viruses, or bovine papilloma virus may be used for delivery of a recombinant GSE into the targeted cell population. Methods which are well known to those skilled in the art can be used to construct recombinant viral vectors containing a GSE sequence operably linked to a promoter that controls its expression (Sambrook et al., 1989, MOLECULAR CLONING: A LABORATORY MANUAL, Cold Spring Harbor Laboratory, N.Y. and Ausubel et al., 1989, CURRENT PROTOCOLS IN MOLECULAR BIOLOGY, Greene Publishing Associates and Wiley Interscience, N.Y.). In a specific embodiment by way of example, GSE sequences were inserted into a retroviral vector. In cases where an adenovirus is used as an expression vector, a GSE sequence may be ligated to an adenovirus transcription-translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing GSE in infected hosts (Logan & Shenk, 1984, *Proc. Natl. Acad. Sci. USA* 81:3655–3659).

Alternatively, recombinant GSE nucleic acid molecules can be reconstituted into liposomes for delivery to target cells. Liposomes are spherical lipid bilayers with aqueous interiors. All molecules that are present in an aqueous solution at the time of liposome formation (in this case, oligonucleotides) are incorporated into this aqueous interior. The liposomal contents are both protected from the external microenvironment and, because liposomes fuse with cell membranes, are efficiently delivered into the cell cytoplasm, obviating the need to neutralize the polynucleotides' negative charge.

Specific initiation signals may also be required for efficient translation of inserted GSE sequences. Exogenous transcriptional control signals, including the ATG initiation codon, must be provided. Furthermore, the initiation codon must be in phase with the reading frame of the GSE sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153: 516–544).

The isolated GSE sequences suppress HIV activity by either encoding protein or RNA products. The present invention encompasses any such protein product, including fusion proteins, leader peptides and localization signals. In addition, anti-sense RNA, DNA molecules and ribozymes that function to inhibit HIV infection are also within the scope of the invention. Anti-sense RNA and DNA molecules act to directly block the translation of mRNA by binding to targeted mRNA and preventing protein translation. GSEs may be represented by structural RNAs which act as decoys.

Some GSEs may also form triplexes. Oligodeoxyribonucleotides can form sequence-specific triple helices by hydrogen bonding to specific complementary sequences in duplexed DNA. Formation of specific triple helices may selectively inhibit the replication and/or gene expression of targeted genes by prohibiting the specific binding of functional trans-acting factors.

Polynucleotides to be used in triplex helix formation should be single stranded and composed of deoxynucleotides. The base composition of these polynucleotides must be designed to promote triple helix formation via Hoogsteen base pairing rules, which generally require sizeable stretches of either purines or pyrimidines to be present on one strand of a duplex. Polynucleotide sequences may be pyrimidine-based, which will result in TAT and CGC triplets across the three associated strands of the resulting triple helix. The pyrimidine-rich polynucleotides provide base complementarity to a purine-rich region of a single strand of the duplex in a parallel orientation to that strand. In addition, polynucleotides may be chosen that are purine-rich, for example, containing a stretch of G residues. These polynucleotides will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" oligonucleotide. Switchback oligonucleotides are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of HIV RNA sequences. GSE represented by antisense RNA showing high affinity binding to target sequences can also be used as ribozymes by addition of enzymatically active sequences known to those skilled in the art.

Both anti-sense RNA and DNA molecules, and ribozymes of the invention may be prepared by any method known in the art. These include techniques for chemically synthesizing oligodeoxyribonucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into host cells.

Various modifications to the nucleic acid molecules may be introduced as a means of increasing intracellular stability and half-life. Possible modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into cells or tissues include the insertion of naked polynucleotide, i.e., by injection into tissue, the introduction of a GSE in a cell ex vivo, i.e., for use in autologous cell therapy, the use of a vector such as a virus, retrovirus, phage or plasmid, etc. or techniques such as electroporation which may be used in vivo or ex vivo.

The GSEs may be formulated and administered through a variety of means, including systemic, localized, or topical administration. Techniques for formulation and administration may be found in "Remington's Pharmaceutical Sciences," Mack Publishing Co., Easton, Pa., latest edition. The mode of administration may be selected to maximize delivery to a desired target site in the body.

For systemic administration, route of injection includes, intramuscular, intravenous, intraperitoneal, and subcutaneous. The polynucleotides of interest are formulated in aqueous solutions, preferably in physiologically compatible buffers such as Hanks's solution, Ringer's solution, or physiological saline buffer. In addition, the polynucleotides may be formulated in solid or lyophilized form, then redissolved or suspended immediately prior to use.

1.7. Uses of GSE to Prevent Tumorigenesis

The present invention also includes GSEs that prevent tumorigenesis. In particular, GSEs, the sequence of which corresponds to the rev gene of HIV. Without being bound by theory, Applicants believe that a GSE corresponding to the rev gene can prevent tumorigenesis because the GSEs may bind to hdm2 protein and prevent its translocation within a cell. Hdm2 protein regulates the stability of the p53 protein. The hdm2 protein translocates between the nucleus and cytoplasm of a cell. Rev protein of HIV uses the same translocation pathway as hdm2. Thus, hdm2 protein, which is involved in tumor formation, apparently depends on a nuclear export pathway that overlaps, or is identical to, that utilized by the HIV Rev protein. Applicants believe that the Rev GSEs of the present invention may prevent the translocation of hdm2, thereby preventing tumorigenesis.

Preferred GSEs to use for preventing tumorigenesis include SEQ ID NO:15 and SEQ ID NO:16, referred to herein as Rev GSEs. Methods to deliver and express GSEs as disclosed herein are applicable to this embodiment. A Rev GSE can be delivered to a cell susceptible to tumor formation either in vivo or in vitro using methods known in the art. Preferably, a Rev GSE nucleic acid sequence is expressed in a cell in the form of a peptide. Cells susceptible to tumor formation include normal cells that are the same cell type as a transformed cell. Transformation refers to the change that a normal cell undergoes as it develops unrestricted growth. Typically, a Rev GSE will be delivered to a cell isolated from a patient having a tumor, in which the cell type of the tumor has been identified thereby enabling identification of susceptible cells.

2. Example

Isolation and Identification of GSE Against HIV-1

2.1. Materials and Methods 2.1.1. Construction of RFE Library

HIV-1 genomic DNA included pBENN7 (Cat. No. 342) derived from 5' half of HIV- $1_{BRU}$ (AIDS Research and Reference Reagent Program, Rockville, Md.) (ARRRP), 9B/6R derived from 3' half of HIV-$1_{SF2}$ and HIV-$1_{HXB2}$ genomic DNA. One RFE library was constructed using HIV-$1_{BRU}$ and HIV-$1_{SF2}$ -derived genomes as the DNA source. A second library was made from HIV-$1_{HXB2}$ genomic DNA. The plasmids were partially digested with DNase I in the presence of manganese (Sambrook et al., 1989, MOLECULAR CLONING: A LABORATORY MANUAL, Cold Spring Harbor Laboratory, N.Y.). Under these conditions, DNase I is known to produce mostly double-stranded breaks. The resulting fragments were repaired with the Klenow fragment of DNA polymerase I and T4 polymerase and ligated to synthetic double-stranded adaptors. The adaptor sequence for the first library contained three ATGs:

5'-GAATTCAAGCTTATGGATGGATG (SEQ ID NO: 26)

For the second library, only one ATG was used:

5'-GATTCAGCTTGCCGCACCATGGCT (SEQ ID NO: 27)

Both libraries used the same 3' primer containing three stop codons:

5'-GGATCCATCGATTCACTCACTCA (SEQ ID NO: 28)

Thereafter, the mixture was digested with BamHI and EcoRI, column purified and ligated to the retroviral vector LXSN (Miller and Rosman, 1989, *BioTechniques* 7:980–990) cut with EcoRI and BamHI. Alternatively, the fragments were ligated to the vector LXSNgfr, which was constructed by replacing the neomycin resistance gene of LXSN with a truncated low affinity nerve growth factor receptor gene. The ligation mixture was transformed into *E. coli*. The total plasmid was purified from ~100,000 recombinant clones. The size distribution of the cloned fragments was tested by PCR amplification using primers derived from the vector sequences adjacent to the adaptors.

2.1.2. Cell Lines and Reagents

The OM10.1 cells are available from the American Type Culture Collection, Rockville, Md. as CRL 10850 (Butera, U.S. Pat. No. 5,256,534). OM10.1 cells were a chronically infected promyelocytic clone of HL-60 which contained a single copy of the HIV-$1_{BRU}$ isolate. The CEM-ss cells are available from the ARRRP as Cat. No. 776. The cells were maintained in RPMI 1640 medium supplemented with 10% fetal bovine serum at 37° C. and 5% $CO_2$. The amphotropic packaging cell line BING was maintained in DMEM supplemented with 10% FBS at 37° C. and 5% $CO_2$. Persistently HIV-infected cells, HUT78/HIV-$1^{SF2}$ and H9/HIV-$1_{IIIB}$ were obtained from ARRRP and used to prepare HIV-$1_{SF2}$ and HIV-$1_{IIIB}$ viral stocks.

The anti-CD4 antibodies, Q4120PE (Sigma, St. Louis, Mo.) and L120 (Becton Dickinson Immunocytometry Systems, San Jose, Calif.), and anti-p24 (KC-57 FITC, Coulter, Hialeah, Fla.) antibodies were purchased. TNF-α was obtained from Boehringer Mannheim. G418 was purchased from Gibco/BRL as neomycin (Gaithersburg, Md.).

2.1.3. Transfection and Transduction

The plasmid DNA prepared according to the method of Section 6.1.1. supra, was transfected into the packaging cell line, BING, using a standard calcium phosphate method. For LXSN-based libraries and GSEs, the packaging cells were co-cultivated with OM10.1 cells or CEM-SS cells for 2–3 hours. Three cocultivations were used at 24,48 and 72 hours after transfection. Cells were then grown under neomycin selection for two weeks. The surviving cells were purified using "FICOLL" and grown in neomycin-free media before any further manipulations. A different method was used for LXSNgfr based libraries and GSEs. Filtered retroviral supernatants from BING cells (24 and 48 hour virus) were used to infect the target cells by centrifugation at 1200×g for 90 minutes. One week later, cells were stained with a NGFR monoclonal antibody and the transduced cells represented by NGFR positive population were sorted using a FACS Vantage (Becton Dickinson) equipped with a 488 nm argon laser. Cells were cultured in media and checked for NGFR prior to use.

2.1.4. Immunofluorescence and Flow Cytometry

For the selection of CD4$^+$ or NGFR$^+$ cells, $10^7$ cells were washed twice with Assay Buffer (500 mL PBS, 1 mL of 0.5 mM of EDTA at pH 8, 0.5 ml of 10% sodium azide and 10 mL of fetal bovine serum), and resuspended in 500 μl PBS to which 50 μl of an anti-CD4 antibody, Q4120PE or L120, or PE-conjugated anti-NGFR antibody 20.4 (ATCC) was added. After incubation at 4° C. for 30 min., 5 mL of Assay Buffer was added and the cells centrifuged at 1200 rpm for 4 min. The cells were washed twice with Assay Buffer before sorting by FACS. The aforementioned procedure was performed under sterile conditions.

In order to determine p24 expression in HIV-infected cells, the cells were first washed twice with Assay Buffer. About $10^6$ cells were suspended in 100 μL Assay Buffer, mixed with 2 ml of Ortho PermeaFix Solution (Ortho Diagnostics, Raritan, N.J.), and incubated for 40 min. at room temperature. After centrifugation at 1200 rpm for 4 min. at room temperature, the cells were resuspended in 2 ml Wash Buffer (500 mL PBS, 25 mL fetal bovine serum, 1.5% bovine serum albumin and 0.0055% EDTA) for 10 min. at room temperature. After centrifugation, the cells were resuspended in 50 μL Wash Buffer and mixed with 1:500 dilution of an $IgG_{2a}$ antibody for 20 min. at room temperature, followed by incubation with 5–10 μL of anti-p24 antibody (KC57-FITC, Coulter, Hialeah, Fla.) for 30 min. at room temperature. The cells were then washed twice with Wash Buffer and analyzed by flow cytometry.

2.1.5. Selection of GSE in OM10.1 Cells

The transduced populations of the OM10.1 cells (GSE library or insert free vector) were washed once with PBS, then induced with 0.1 ng/mL of TNF-α (Boehringer Mannheim, Indianapolis, Ind.) in RPMI supplemented with 10% FBS at a density 5×$10^5$ cells/ml. After 24 hours, cells were stained with a PE-conjugated anti-CD4 monoclonal antibody. Propidium iodide was added to a final concentration of 10 μg/mL immediately prior to sorting. The propidium iodide negative, CD4 positive population was sorted by flow cytometry. The cells were lysed and the genomic DNA was purified. Inserts were amplified by PCR using vector-derived primers, the mixture was digested with BamHI and EcoRI, column purified, ligated to BamHI/EcoRI digested vector, and transformed into *E. coli*. Purified DNA from transformants were either used as a pool for subsequent rounds of selection and/or individually isolated and sequenced using the ALF DNA Sequencer (Pharmacia LKB, Piscataway, N.J.).

2.1.6. Productive Infection Selection of GSE

Transduced CEM-ss cells (GSE library or insert free vector) were infected with HIV-$1_{IIIB}$ at a tissue culture infectious doses ($TCID_{50}$) of 3000 per $10^6$ cells in the presence of polybrene. At 9 days post infection, $10^7$ cells were stained for CD4 and p24. The p24 negative, CD4 positive population was sorted. Genomic DNA purification, insert amplification and subcloning were performed as described above.

2.1.7. Recovery of GSE and Sequence Analysis

Genomic DNA was isolated from the selected population of OM10.1 cells or CEM cells harboring putative GSE by resuspending the cell pellet in 0.1% Triton X-100, 20 μg/mL proteinase K in 1×PCR buffer, incubating at 55° C. for 1 hour, and boiling for 10 minutes. Genomic DNA was used for PCR amplification using vector-derived primers, cloned into the LXSN vector, and transformed into *E. coli* using techniques well known in the art. Individual plasmids were purified from *E. coli* clones using QIAGEN plasmid kits. Inserts were sequenced by the dideoxy procedure (AutoRead Sequencing Kit, Pharmacia Biotech) and run on a Pharmacia LKB A.L.F. DNA sequencer. Sequences were analyzed using the DNASTAR program.

2.2. Results

The HIV-1 life cycle consists of two distinct stages: productive or acute infection and latency. An ideal HIV inhibitor should be effective against both stages. Accordingly, two selection approaches of HIV-1 GSEs were developed. The first approach, designed to inhibit virus induction in latently infected cells, was based on the unique properties of OM10.1 cells. For selection of GSEs in OM10.1 cells, an HIV-1 RFE library was constructed from plasmids containing the genome of the virus. Following transfection of the entire library into a packaging cell line, virus was transferred into OM10.1 cells by co-cultivation. The virally-transduced cells were selected in culture medium containing G-418 to ensure the retention of the viral vector.

Figure 2:
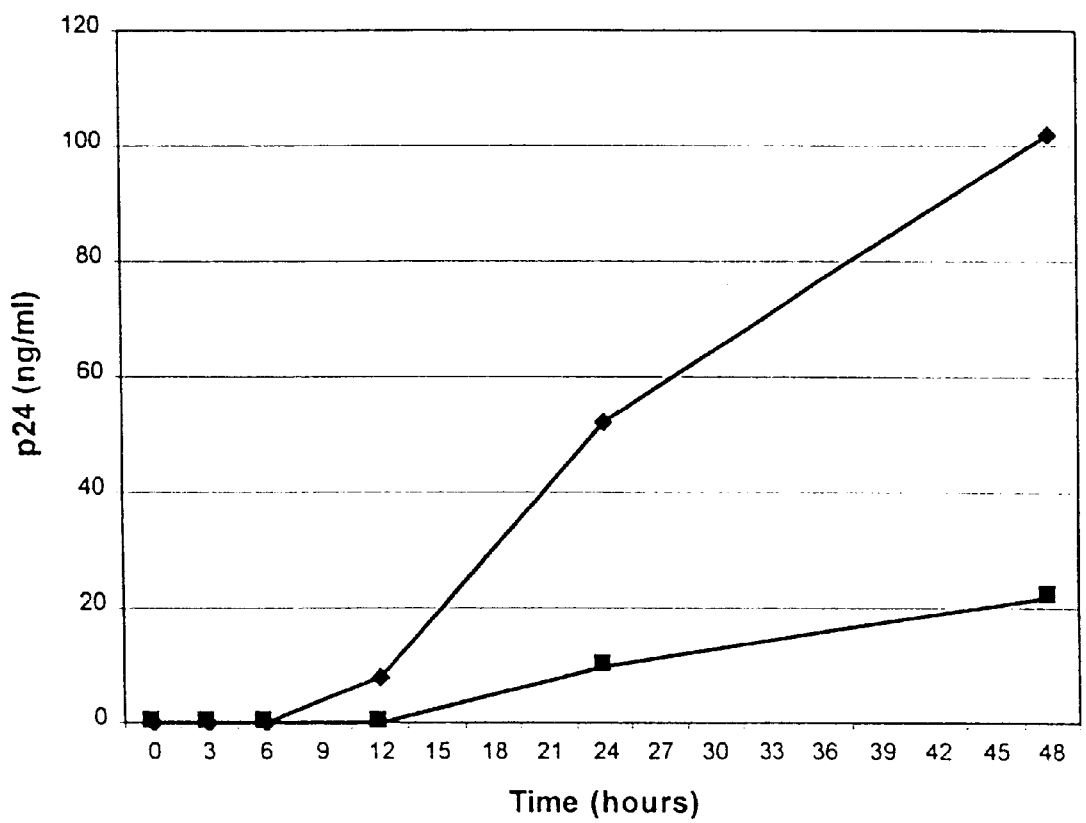
FIG. 2. HIV p24 level increases in OM10.1 cells after TNF-α induction; TNF-induced cells, -♦-; uninduced cells, -■-.

When the transduced OM10.1 cells were treated with TNF-α and stained with an antibody specific for the cell surface molecule CD4, a rapid loss of CD4 expression was observed in about 90% of the cells (FIG. 1). In contrast, approximately 99% of the uninduced OM10.1 cells retained CD4 expression. It is believed that activation of the latent virus in OM10.1 cells by TNF-α led to the production of viral protein gp160/120, which bound to cytoplasmic CD4, thereby preventing its cell surface translocation. A diminution of CD4$^+$ OM10.1 cells also correlated with an increased production of viral protein p24 in the cells following TNF-α induction (FIG. 2).

Based on these findings, expression of a GSE capable of interfering with induction was expected to result in the retention of surface CD4 by OM10.1 cells. The small number of residual CD4$^+$ cells were stained with an anti-CD4 antibody and sorted by FACS. After the cells were expanded in culture, the individual GSE polynucleotides were recovered by PCR amplification and their nucleotide sequences determined.

The second selection scheme was designed to select GSEs capable of inhibiting productive HIV infection. Replication of HIV in susceptible cells is associated with accumulation of intracellular p24, concomitant with down-modulation of surface CD4. For productive infection selection, an HIV-1 RFE library was constructed from plasmids containing the genome of the virus. The entire library was transfected into CEM-ss cells. The cells were infected with HIV-1$_{IIIB}$ and sorted by flow cytometry for CD4 positive, p24 negative cells.

RFE libraries from various HIV-1 isolates were cloned into retroviral vectors. A library from isolates HIV-1$_{BRU}$ and HIV-1$_{SF2}$ in LXSN vector was used in OM10.1 selection. A library from HIV-1$_{HXB2}$ in LXSN vector was used in productive infection selection. A third library from HIV-1 $_{HXB2}$ in LXSNgfr vector was used in two independent experiments in OM10.1 cells. Each RFE library was transferred into the target cells (OM10.1 or CEM-ss) and two rounds of selection were performed. The reproducibility of the system was demonstrated by independent transfers and selections of the same RFE library. After the second round of selection in OM10.1 cells, 40–50% of the elements were from a few short regions of the HIV-1 genome, indicating selection for these sequences. Sequence comparison of individual elements enriched in all selections revealed 7 clusters of overlapping sequences, 5 in the sense orientation and 2 in the antisense orientation (FIG. 3). Two clusters are from areas of the HIV-1 genome where two or more viral genes overlap (vpr/tat, rev/tat, env/nef). Some elements were nearly identical to those isolated in the productive infection selection. Thus, three clusters (the nef sense cluster, the rev/tat sense cluster, and the vpr/tat antisense cluster) were identified in all libraries and selections. A cluster of sense-oriented elements from the reverse transcriptase (RT) gene was found only in the productive infection selection, presumably because reverse transcription preceded integration. SEQ ID NOS: 1–25 present nucleotide sequences of the selected polynucleotides which corresponded to GSEs in either sense or antisense orientation. More specifically, GSE IGX-149 in SEQ ID NO:1 is in the gag (p24) sense orientation. IGX 104 (SEQ ID NO:2), IGX-109 (SEQ ID NO:3) and IGX-102 (SEQ ID NO:4) are in the pol (reverse transcriptase) sense orientation. IGX-111 (SEQ ID NO:5), IGX-013 (SEQ ID NO:6), IGX-018 (SEQ ID NO:7), IGX-117 (SEQ ID NO:8), IGX-217 (SEQ ID NO:9) and IGX-050 (SEQ ID NO:10) are in vpr/tat sense orientation. IGX-120 (SEQ ID NO:11), IGX-108 (SEQ ID NO:12), IGX-031 (SEQ ID NO:13) and IGX-201 (SEQ ID NO:14) are in RRE antisense orientation. IGX-103 (SEQ ID NO:15) and IGX-171 (SEQ ID NO:16) are in rev/tat sense orientation. IGX-222 (SEQ ID NO:17), IGX-003 (SEQ ID NO:18), IGX-219 (SEQ ID NO:19), IGX-210 (SEQ ID NO:20), IGX-221 (SEQ ID NO:21) and IGX-151 (SEQ ID NO:22) are in env/nef antisense orientation. IGX-078 (SEQ ID NO:23), IGX-121 (SEQ ID NO:24) and IGX-140 (SEQ ID NO:25) are in nef sense orientation.

The fact that GSEs with overlapping sequences from narrowly defined regions of the HIV-1 genome were isolated in different selection systems using different HIV-1 isolates indicates that these GSEs are from functionally important and conserved regions of the viral genome. Surprisingly, clusters of GSEs from previously untargeted regions (RT and nef) were also isolated.

GSEs from the first OM10.1 selection were further tested for their ability to prevent HIV-1 induction by TNF-α. After induction, negative controls (OM10.1 cells and OM10.1 cells with the LXSN vector) revealed background levels of 10% CD4 positive cells (FIG. 4). Two additional negative controls containing anonymous DNA inserts from plasmid vectors (#34 and #220) were 8–11% CD4 positive. However, individual GSE showed a constant and reproducible inhibitory effect by allowing 18–26% of the transduced cells to retain CD4 upon induction with TNF-α (FIG. 4). In contrast OM10.1 cells containing the transdominant mutant, RevM 10 (Malin et al., 1989, Cell 58:205), were not effective at inhibiting induction of virus from latency.

GSEs isolated by OM10.1 selection were tested for their ability to protect uninfected human T cells from a productive HIV-1 infection. Plasmids containing each of these sequences were transferred into CEM-ss cells followed by G418 selection. The Rev transdominant mutant, RevM 10 and a LXSN vector containing an irrelevant piece of plasmid DNA (#34) were used as controls. The G418 resistant cells were 99% CD4$^+$, and were then infected with low titers (TCID$_{50}$ of 500–1000) of HIV-1$_{SF2}$ or high titers (TCID$_{50}$ of 3000) of HIV-1$_{IIIB}$. The cells were removed at various days after infection, and stained with a fluorescein-labeled anti-p24 antibody as an indicator of HIV infection.

Figure 5A:
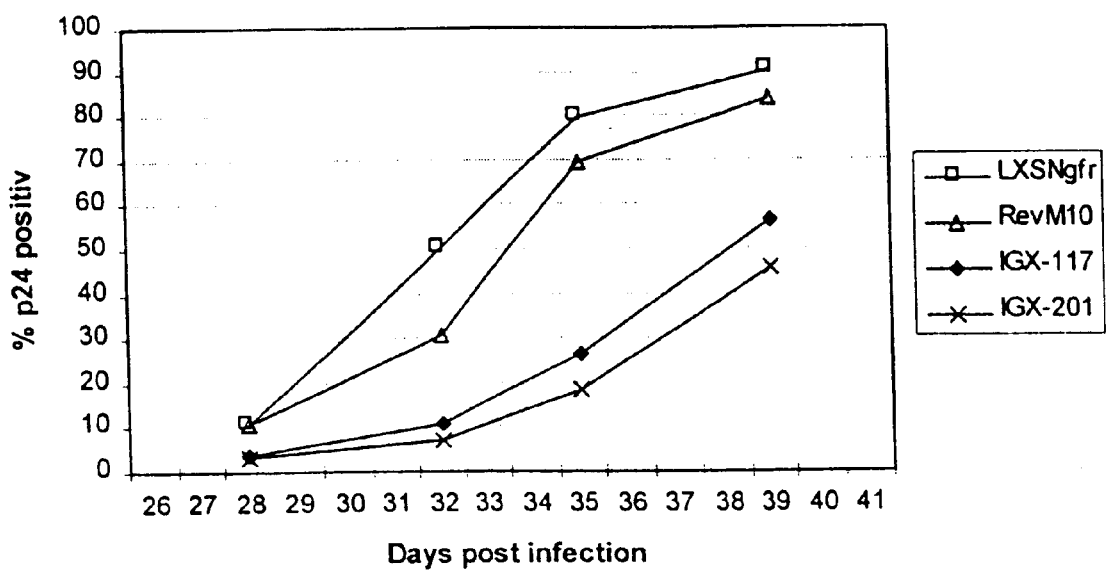
FIG. 5A & B. Time course of viral infection of CEM-ss cells containing GSEs. Results are presented as the percentage of p24 positive cells at specified days post infection. All results are of a representative experiment.
Figure 5B:
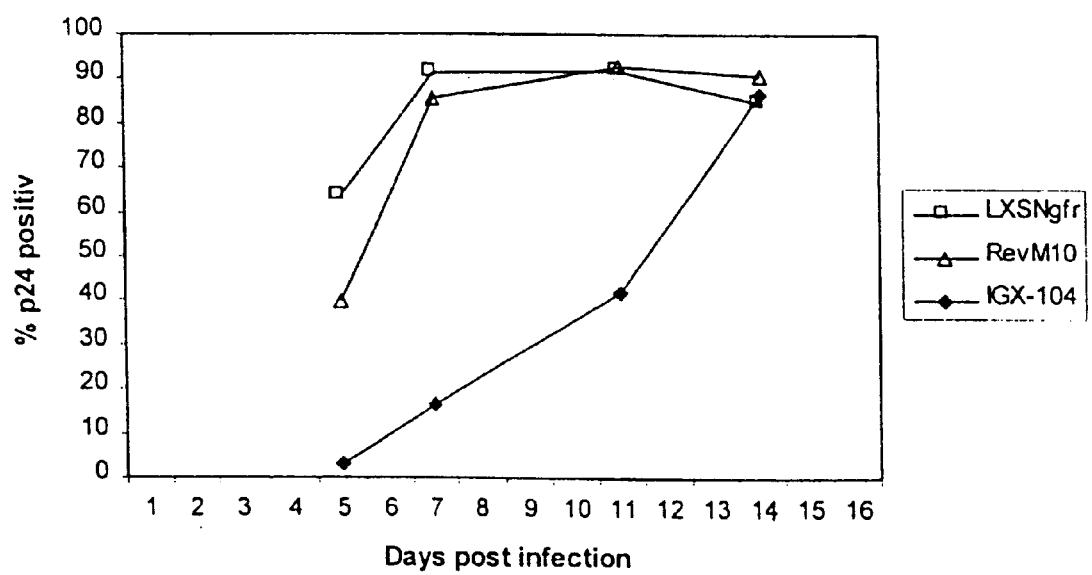
FIG. 5B: CEM-ss cells containing IGX-104 (RT sense, SEQ ID NO:2) and controls were infected with a $TCID_{50}$ of 3000 of HIV-$1_{IIIB}$.

Upon infection with HIV-$^1$$_{SF2}$, a significant delay was observed in the development of the productive infection as determined by intracellular p24 staining (FIG. 5A). GSEs isolated in productive infection selection had sequences overlapping with those from the OM10.1 selection and had similar effects upon viral challenge. The RT cluster of elements isolated in productive infection selection showed inhibitory effects when challenged with HIV-1$_{IIIB}$ (FIG. 5B).

In all infections, the GSEs demonstrated similar or better inhibitory effects than the transdominant mutant, RevM10, a known inhibitor of HIV-1 replication in T cells.

In conclusion, a large number of GSEs have been isolated from the HIV-1 genome based on their ability to maintain CD4 expression in OM10.1 cells after activation of latent HIV by induction with TNF-α or based on their ability to inhibit productive HIV infection in CEM-ss cells. The isolated GSEs contain nucleotide sequences in both sense and anti-sense orientations, and are mapped to different regions of the HIV-1 genome. Several elements corresponding to portions of the integrase, Nef and Rev/Tat genes are able to suppress HIV-1 infection of T cells by reducing p24 levels in infected cells. Such polynucleotides are useful in protecting the infection by and/or suppressing the replication of HIV-1 in human host cells.

3. Example

Isolation and Identification of GSE Against HIV-1

The methods generally described in Stauber et al. ,1998, *Virology* 251:38–48, are used to determine if GSEs IGX-103 and IGX-171 sequences can inhibit the translocation of hdm2 protein in a cell. IGX-103 and IGX-171 are ligated into retroviral vectors to create an IGX-103 recombinant molecule and an IGX-171 recombinant molecule. A fusion protein is created that comprises hdm2 protein fused to green fluorescent protein (hdm2-GFP). Cells expressing hdm2-GFP fusion protein are transfected with IGX-103 recombinant molecule or IGX-171 recombinant molecule. Confocal microscopy is used to determine whether transport of hdm2-GFP protein between the nucleus and the cytoplasm of the cell is inhibited by expression of the GSE. The observations using cells transfected with GSE are compared with cells transfected with retroviral vector alone.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of inhibiting tumorigenesis, comprising contacting a cell with an isolated polynucleotide comprising a nucleic acid sequence which hybridizes under highly stringent conditions to a nucleic acid comprising a nucleotide sequence complementary to any one of SEQ ID NO:15 or SEQ ID NO:16, wherein said isolated polynucleotide is operably linked to a regulatory sequence, and expression of said isolated polynucleotide in a host cell inhibits hdm2 translocation.

2. The method of claim 1, wherein said polynucleotide is contained in a recombinant vector.

3. The method of claim 1, wherein said polynucleotide is contained in an expression vector.

4. A method of preventing tumor cell formation in a subject, comprising administering to said subject a therapeutically effective amount of an isolated polynucleotide comprising a nucleic acid sequence which hybridizes under highly stringent conditions to a nucleic acid comprising a nucleotide sequence complementary to any one of SEQ ID NO:15 or SEQ ID NO:16, wherein said isolated polynucleotide is operably linked to a regulatory sequence, and expression of said isolated polynucleotide in a host cell inhibits hdm2 translocation.

5. The method of claim 4, wherein said polynucleotide is contained in a recombinant vector.

6. The method of claim 4, wherein said polynucleotide is contained in an expression vector.

* * * * *

SEQUENCE LISTING

<160> NUMBER OF SEQ ID NOS: 28

<210> SEQ ID NO 1
<211> LENGTH: 60
<212> TYPE: DNA
<213> ORGANISM: Human immunodeficiency virus

<400> SEQUENCE: 1
atgacaaata atccacctat cccagtagga gaaatttata aaagatggat aatcctggga        60

<210> SEQ ID NO 2
<211> LENGTH: 86
<212> TYPE: DNA
<213> ORGANISM: Human immunodeficiency virus

<400> SEQUENCE: 2
gggttaaaaa agaaaaaatc agtaacagta ctggatgtgg gtgacgcata tttttcagtt        60
cccttagatg aagacttcag gaaata                                             86

<210> SEQ ID NO 3
<211> LENGTH: 77
<212> TYPE: DNA
<213> ORGANISM: Human immunodeficiency virus

<400> SEQUENCE: 3
aaaaagaaaa aatcagtaac agtactggat gtgggtgacg catatttttc agttccctta        60
gatgaagact tcaggaa                                                       77

<210> SEQ ID NO 4
<211> LENGTH: 67
<212> TYPE: DNA
<213> ORGANISM: Human immunodeficiency virus

<400> SEQUENCE: 4
cagtaacagt actggatgtg ggtgacgcat attttcagt tcccttagat gaagacttca        60
ggaaata                                                                  67

<210> SEQ ID NO 5
<211> LENGTH: 216
<212> TYPE: DNA
<213> ORGANISM: Human immunodeficiency virus

<400> SEQUENCE: 5

| gaattctgca acaactgctg tttatccatt tcagaattgg gtgtcgacat agcagaatag | 60 |
| gcgttactca acagaggaga gcaagaaatg gagccagtag atcctagact agagccctgg | 120 |
| aagcatccag gaagtcagcc taaaactgct tgtaccactt gctattgtaa aaagtgttgc | 180 |
| tttcattgcc aagtttgttt cacaacaaaa gcctta | 216 |

<210> SEQ ID NO 6
<211> LENGTH: 144
<212> TYPE: DNA
<213> ORGANISM: Human immunodeficiency virus

<400> SEQUENCE: 6

| gaattctgca acaactgctg tttatccatt tcagaattgg gtgtcgacat agcagaatag | 60 |
| gcgttactca acagaggaga gcaagaaatg gagccagtag atcctagact agagccctgg | 120 |
| aagcatccag gaagtcagcc taaa | 144 |

<210> SEQ ID NO 7
<211> LENGTH: 184
<212> TYPE: DNA
<213> ORGANISM: Human immunodeficiency virus

<400> SEQUENCE: 7

| gaattctgca acaactgctg tttatccatt tcagaattgg gtgtcgacat agcagaatag | 60 |
| gcgttactca acagaggaga gcaagaaatg gagccagtag atcctagact agagccctgg | 120 |
| aagcatccag gaagtcagcc taaaactgct tgtaccactt gctattgtaa aaagtgttgc | 180 |
| tttc | 184 |

<210> SEQ ID NO 8
<211> LENGTH: 94
<212> TYPE: DNA
<213> ORGANISM: Human immunodeficiency virus

<400> SEQUENCE: 8

| gaattctgca acaactgctg tttatccatt tcagaattgg gtgtcgacat agcagaatag | 60 |
| gcgttactca acagaggaga gcaagaaatg gagc | 94 |

<210> SEQ ID NO 9
<211> LENGTH: 92
<212> TYPE: DNA
<213> ORGANISM: Human immunodeficiency virus

<400> SEQUENCE: 9

| gaattctgca acaactgctg tttatccatt tcagaattgg gtgtcgacat agcagaatag | 60 |
| gcgttactca acagaggaga gcaagaaatg ga | 92 |

<210> SEQ ID NO 10
<211> LENGTH: 179
<212> TYPE: DNA
<213> ORGANISM: Human immunodeficiency virus

<400> SEQUENCE: 10

-continued acaactgctg tttatccatt tcagaattgg gtgtcgacat agcagaatag gcgttactca        60
acagaggaga gcaagaaatg gagccagtag atcctagact agagccctgg aagcatccag       120
gaagtcagcc taaaactgct tgtaccactt gctattgtaa aaagtgttgc tttcattgc        179

<210> SEQ ID NO 11
<211> LENGTH: 104
<212> TYPE: DNA
<213> ORGANISM: Human immunodeficiency virus

<400> SEQUENCE: 11
ggattcttgc ctggagctgc ttgatgcccc agactgtgag ttgcaacaga tgctgttgcg        60
cctcaatagc cctcagcaaa ttgttctgct gctgcactat acca                       104

<210> SEQ ID NO 12
<211> LENGTH: 69
<212> TYPE: DNA
<213> ORGANISM: Human immunodeficiency virus

<400> SEQUENCE: 12
cccagactgt gagttgcaac agatgctgtt gcgcctcaat agccctcagc aaattgttct        60
gctgctgca                                                                69

<210> SEQ ID NO 13
<211> LENGTH: 83
<212> TYPE: DNA
<213> ORGANISM: Human immunodeficiency virus

<400> SEQUENCE: 13
tgttgatcct ttaggtatct ttccacagcc aggattcttg cctggagctg cttgatgccc        60
cagactgtga gttgcaacag atg                                                83

<210> SEQ ID NO 14
<211> LENGTH: 91
<212> TYPE: DNA
<213> ORGANISM: Human immunodeficiency virus

<400> SEQUENCE: 14
atccccagga gctgttgatc ctttaggtat ctttccacag ccaggattct tgcctggagc        60
tgcttgatgc cccagactgt gagttgcaac a                                       91

<210> SEQ ID NO 15
<211> LENGTH: 124
<212> TYPE: DNA
<213> ORGANISM: Human immunodeficiency virus

<400> SEQUENCE: 15
ggcccgacgg aatcgaagaa gaaggtggag agagacagag acagatccgt tcgattagtg        60
tatggattct tagcacttat ctgggaagat ctgcggagcc tgtgcctctt cagctaccgc       120
cgct                                                                   124

<210> SEQ ID NO 16
<211> LENGTH: 71
<212> TYPE: DNA
<213> ORGANISM: Human immunodeficiency virus

<400> SEQUENCE: 16
ggcccgaagg aatagaagaa gaaggtggag agagagacag agacagatcc attcgattag        60
tgaacggatc c                                                            71

<210> SEQ ID NO 17
<211> LENGTH: 339
<212> TYPE: DNA
<213> ORGANISM: Human immunodeficiency virus

<400> SEQUENCE: 17

| tgtattgcta | cttgtgattg | ctccatgttt | ttccaggtct | cgagatgctg | ctcccacccc | 60 |
| atctgctgct | ggctcagctc | gtctcattct | tcccttaca | gtaggccatc | caaccacact | 120 |
| acttttgac  | cacttgccac | ccatcttata | gcaaaatcct | ttccaagccc | tgtcttattc | 180 |
| ttctaggtat | gtggcgaata | gctctacaag | ctccttgtac | tacttctata | accctatctg | 240 |
| tcccctcagc | tactgctatg | gctgtggcat | tgagcaagct | aacagcacta | ttctttagtt | 300 |
| cctgactcca | atactgtagg | agattggagg | aatatttga  |            |            | 339 |

<210> SEQ ID NO 18
<211> LENGTH: 339
<212> TYPE: DNA
<213> ORGANISM: Human immunodeficiency virus

<400> SEQUENCE: 18

| caggcacaag | cagcattggt | agctgctgta | ttgctacttg | tgattgctcc | atgttttcc  | 60 |
| aggtctcgag | atgctgctcc | caccccatct | gctgctggct | cagctcgtct | cattctttcc | 120 |
| cttacagtag | gccatccaac | cacactactt | tttgaccact | tgccacccat | cttatagcaa | 180 |
| aatcctttcc | aagccctgtc | ttattcttct | aggtatgtgg | cgaatagctc | tacaagctcc | 240 |
| ttgtactact | tctataaccc | tatctgtccc | ctcagctact | gctatggctg | tggcattgag | 300 |
| caagctaaca | gcactattct | ttagttcctg | actccaata  |            |            | 339 |

<210> SEQ ID NO 19
<211> LENGTH: 103
<212> TYPE: DNA
<213> ORGANISM: Human immunodeficiency virus

<400> SEQUENCE: 19

| aaatcctttc | caagccctgt | cttattcttc | taggtatgtg | gcgaatagct | ctacaagctc | 60 |
| cttgtactac | ttctataacc | ctatctgtcc | cctcagctac | tgc        |            | 103 |

<210> SEQ ID NO 20
<211> LENGTH: 112
<212> TYPE: DNA
<213> ORGANISM: Human immunodeficiency virus

<400> SEQUENCE: 20

| acttttgac  | cacttgccac | ccatcttata | gcaaaatcct | ttccaagccc | tgtcttattc | 60 |
| ttctaggtat | gtggcgaata | gctctacaag | ctccttgtac | tacttctata | ac         | 112 |

<210> SEQ ID NO 21
<211> LENGTH: 113
<212> TYPE: DNA
<213> ORGANISM: Human immunodeficiency virus

<400> SEQUENCE: 21

| tcctcctctt | gtgcttctag | ccaggcacaa | gcagcattgg | tagctgctgt | attgctactt | 60 |
| gtgattgctc | catgttttc  | caggtctcga | gatgctgctc | cacccccatc | tgc        | 113 |

<210> SEQ ID NO 22

```
<211> LENGTH: 339
<212> TYPE: DNA
<213> ORGANISM: Human immunodeficiency virus

<400> SEQUENCE: 22
tgtattgcta cttgtgattg ctccatgttt ttccaggtct cgagatgctg ctcccacccc      60
atctgctgct ggctcagctc gtctcattct ttcccttaca gtaggccatc caaccacact     120 acttttgac cacttgccac ccatcttata gcaaaatcct ttccaagccc tgtcttattc      180
ttctaggtat gtggcgaata gctctacaag ctccttgtac tacttctata acctatctg     240 tccctcagc tactgctatg gctgtggcat tgagcaagct aacagcacta ttctttagtt     300
cctgactcca atactgtagg agattggagg aatatttga                           339

<210> SEQ ID NO 23
<211> LENGTH: 91
<212> TYPE: DNA
<213> ORGANISM: Human immunodeficiency virus

<400> SEQUENCE: 23
tgggagcagt atctcgagac ctggaaaaac atggagcgat cacaagtagc aatacagcag      60
ctactaatgc tgattgtgcc tggctagaag c                                    91

<210> SEQ ID NO 24
<211> LENGTH: 82
<212> TYPE: DNA
<213> ORGANISM: Human immunodeficiency virus

<400> SEQUENCE: 24
cgagacctgg aaaaacatgg agcaatcaca gtagcaata cagcagctac caatgctgct       60
tgtgcctggc tagaagcaca ag                                              82

<210> SEQ ID NO 25
<211> LENGTH: 79
<212> TYPE: DNA
<213> ORGANISM: Human immunodeficiency virus

<400> SEQUENCE: 25
aagtagcaat acagcagcta ccaatgctgc ttgtgcctgg ctagaagcac aagaggagga      60
ggaggtgggt tttccagtc                                                  79

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 26
gaattcaagc ttatggatgg atg                                             23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 27
gattcagctt gccgcaccat ggct                                            24
```

```
<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 28
ggatccatcg attcactcac tca                                              23
```